United States Patent [19]

Shankar et al.

[11] Patent Number: 5,334,603
[45] Date of Patent: Aug. 2, 1994

[54] COMPOSITION AND USE OF 3-PHENYL-5-THIOCYANO-METHYLTHIO-1,3,4-THIADIAZOLE-2(3H)THIONE

[75] Inventors: Ravi B. Shankar; R. Garth Pews; Duane R. Romer, all of Midland, Mich.

[73] Assignee: The Dow Chemical Company, Midland, Mich.

[21] Appl. No.: 153,703

[22] Filed: Nov. 16, 1993

[51] Int. Cl.$^5$ ............ C07D 285/125; A61K 31/425; A01N 43/82
[52] U.S. Cl. ...................... 514/363; 548/142
[58] Field of Search .................. 548/142; 514/363

[56] References Cited

U.S. PATENT DOCUMENTS

| | | | |
|---|---|---|---|
| 2,331,749 | 6/1938 | Watt | 548/142 |
| 2,677,690 | 2/1952 | Goshorn et al. | 548/142 |
| 2,799,651 | 7/1957 | Richardson et al. | 548/142 |
| 3,337,398 | 8/1967 | Kier | 514/363 |
| 3,753,999 | 8/1970 | Tempel et al. | 260/386.6 |
| 3,910,791 | 10/1975 | Konig et al. | 96/76 |
| 4,094,880 | 6/1978 | Goralski | 260/302 |
| 4,097,669 | 6/1978 | Reisdorff et al. | 542/413 |
| 4,143,043 | 3/1979 | Goralski et al. | 260/302 |
| 4,880,729 | 11/1989 | Heki et al. | 430/410 |
| 4,952,580 | 8/1990 | Martinez et al. | 514/236.2 |
| 4,966,836 | 10/1990 | Inoue et al. | 430/598 |

OTHER PUBLICATIONS

J. R. Geigy, Chemical Abstracts, vol. 60, 1764, (FR. 1,335,755), "O, O-Dialkyl S-[5-alkylthio (or alkoxy)-1,3,4-Thiadiazol-2(3H)-on (or thion)-3-ylmethyl]-thioloThionophosphates".

A. G. M. Willems et al., 90, (1971) Recueil, pp. 97–104, "The Chemistry and Fungicidal and Phytotoxic Properties of Heterocyclic Sulfonyl-, Sulfinyl-, and Thio-Methyl Thiocyanates".

P. Ray et al., Chemical Abstracts, vol. 14, 1298, (J. Chem. Soc, 115, 1308-12 (1919)), "Reaction of the Potassium Salts of 2-thiol-5-thio-4-phenyl-4,5-dihydro-1,3,4-thiodiazole, etc.".

Primary Examiner—Richard L. Raymond
Assistant Examiner—S. Mark Clardy
Attorney, Agent, or Firm—Ronald G. Brookens; S. Preston Jones

[57] ABSTRACT

A compound is prepared which corresponds to the formula:

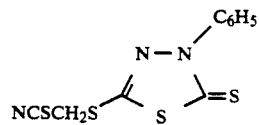

This compound has been found to exhibit antimicrobial activity in industrial and commercial applications and compositions containing this compound are so employed.

5 Claims, No Drawings

COMPOSITION AND USE OF 3-PHENYL-5-THIOCYANO-METHYLTHIO-1,3,4-THIADIAZOLE-2(3H)THIONE

BACKGROUND OF THE INVENTION

The field of this invention is a novel compound which is useful as an antimicrobial agent.

The desirability of identifying or discovering new antimicrobial agents is widely recognized. New agents are desired for several reasons; these include, but are not limited to, responding to the problem created by the development of microbe strains resistant to known agents, the occurrence of undesirable interactions of certain known agents with the medium or product in which the agent is used, and high toxicity of certain known agents to certain non-target organisms such as mammals.

SUMMARY OF THE INVENTION

The present invention is a compound corresponding to the formula:

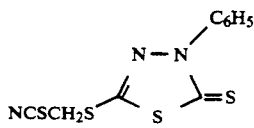

The invention further contemplates:

An antimicrobial composition comprising an inert diluent and an antimicrobially-effective amount of a compound corresponding to Formula I;

a method for inhibiting microorganisms in a microbial habitat comprising contacting said microbial habitat with an antimicrobially-effective amount of a compound corresponding to Formula I; and use of the compound corresponding to Formula I as a microorganism inhibitor.

The compound, 3-phenyl-5-thiocyanomethylthio-1,3,4-thiadiazole-2(3H)thione is prepared by slurrying 5-mercapto-3-phenyl-1,3,4-thiadiazole-2(3H)-thione potassium salt (5.2 g, 0.02 mol) in bromochloromethane (20 ml) containing tetrabutyl ammonium bromide (0.1 g) and stirring the slurry for 6 hours. The reaction mixture was then diluted with methylene chloride and washed with water, dried and concentrated under reduced pressure. The residue was dissolved in dimethylformamide (75 ml) and potassium thiocyanate (2.5 g) was added and heated to 75° C. for 10 hours. The reaction mixture was diluted with methylene chloride and washed with water, dried and concentrated under reduced pressure to yield 3.7 g (62%) of a yellow solid having a melting point of 113°-114° C. The structural formula of this solid material, as confirmed by NMR and MS, is:

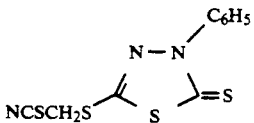

The starting material, 5-mercapto-3-phenyl, 1,3,4-thiadiazole-2(3H)thione potassium salt, is an article of commerce available from Lancaster Synthesis Inc., Cat #8599.

Antimicrobial Activity

The compound of this invention is useful as an antimicrobial additive to such industrial products as marine antifoulants, wood preservatives, styrene-butadiene latexes used for paper coatings, paints, inks, adhesives, soaps, cutting oils, textiles, and paper and pigment slurries. The compound is also useful as an antimicrobial additive in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, the compound disclosed herein is not active at the same concentration against different microbial species. That is, there is some species-to-species variation in antimicrobial potency and spectrum of antimicrobial activity.

The present invention is also directed to a method for inhibiting microorganisms which comprises contacting said microorganisms or habitat thereof with an antimicrobially effective amount of the compound of this invention.

The antimicrobial compound of this invention may be added directly to aqueous formulations susceptible to microbial growth, either undiluted or dissolved in inert diluents such as organic solvents such as glycols, alcohols, or acetone. The compound may also be added alone or in combination with other preservatives.

As used herein, the term "microorganism" is meant to refer to bacteria, fungi, viruses, algae, subvital agents and protozoa.

As used herein, the term "antimicrobially-effective amount" refers to that amount of the compound, or of a composition comprising such compound, of this invention needed to exhibit inhibition of selected microorganisms. Typically, this amount varies from providing about 1 part per million (ppm) to about 5,000 ppm by weight of the compound to a microbial habitat being contacted with the compound. Such amounts vary depending upon the particular habitat and microorganism treated. Also, the exact concentration of the compound to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", or "inhibit" or "inhibiting" or the like refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

The minimum inhibitory concentration (MIC) for the compound is determined for 9 bacteria, using nutrient agar; and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respective American Type Culture Collection (ATCC) identification numbers.

TABLE 1

| Organisms used in the Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida Albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

Tables II and III, the MIC values of the compound as compared to the MIC of a standard commercial preservative (with 1-(3-chloroallyl)-3,5,7,-triaza-1-azoniaadamantane chloride as the active agent, and referred to in Tables II and III as "STANDARD") is set forth for the bacteria organisms and yeast/fungi organisms which are listed in Table I.

TABLE II

Minimum Inhibitory Concentrations for Test Compounds in Bacteria Species (in ppm)

| Compound | ORGANISMS | | | | | | | | |
|---|---|---|---|---|---|---|---|---|---|
| | Bs | Ea | Ec | Kp | Pv | PRD | Pa | Sc | Sa |
| STANDARD | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| INVENTION | | | | | | | | | |
| pH 6.8 | 100 | 100 | 100 | 100 | 100 | 50 | 50 | 100 | 100 |
| pH 8.2 | <10 | >500 | 500 | 250 | 250 | 100 | 50 | 500 | 250 |

TABLE III

Minimum Inhibitory Concentrations for Test Compounds in Yeast/Fungi Species (in ppm) (pH 5.5)

| Compound | ORGANISMS | | | | | | |
|---|---|---|---|---|---|---|---|
| | An | Ca | Pc | Sc | Tv | Ap | Fo |
| STANDARD | >500 | >500 | >500 | 500 | >500 | >500 | >500 |

TABLE III-continued

| | Minimum Inhibitory Concentrations for Test Compounds in Yeast/Fungi Species (in ppm) (pH 5.5) | | | | | | |
|---|---|---|---|---|---|---|---|
| | ORGANISMS | | | | | | |
| Compound | An | Ca | Pc | Sc | Tv | Ap | Fo |
| INVENT. | 5 | 25 | 2.5 | 5 | 25 | 2.5 | 10 |

What is claimed is:

1. A compound corresponding to the formula:

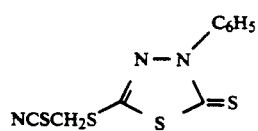

2. An antimicrobial composition comprising an inert diluent and an antimicrobially-effective amount of a compound corresponding to the formula:

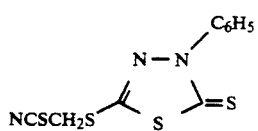

3. The composition of claim 2 wherein the compound is present in the composition in an amount to provide from about 1 part per million to about 5,000 parts per million by weight of the compound to a microbial habitat that is contacted with the composition.

4. A method for inhibiting microorganisms in an microbial habitat comprising contacting said microbial habitat with an antimicrobially-effective amount of a compound corresponding to the formula:

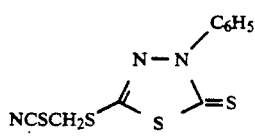

5. The method of claim 4 wherein the compound is used in an amount to provide from about 1 part per million to about 5,000 parts per million by weight of the compound to a microbial habitat being contacted with the composition.

* * * * *